United States Patent
Baker

(10) Patent No.: US 8,753,059 B2
(45) Date of Patent: Jun. 17, 2014

(54) AUTOMATED ROBOTIC SYSTEM FOR SURGICAL INSTRUMENT STORAGE AND RETRIEVAL

(71) Applicant: Robotic Systems & Technologies, Inc., Bronx, NY (US)

(72) Inventor: Russell Baker, Sunnyside, NY (US)

(73) Assignee: Robotic Systems & Technologies, Inc., Bronx, NY (US)

( * ) Notice: Subject to any disclaimer, the term of this patent is extended or adjusted under 35 U.S.C. 154(b) by 0 days.

(21) Appl. No.: 13/706,734

(22) Filed: Dec. 6, 2012

(65) Prior Publication Data

US 2013/0164103 A1 Jun. 27, 2013

Related U.S. Application Data

(63) Continuation of application No. PCT/US2011/040483, filed on Jun. 15, 2011.

(60) Provisional application No. 61/355,652, filed on Jun. 17, 2010.

(51) Int. Cl.
*B25J 13/06* (2006.01)

(52) U.S. Cl.
USPC ........................................ 414/269; 211/85.13

(58) Field of Classification Search
USPC .................. 414/266–269; 206/370; 211/85.13
See application file for complete search history.

(56) References Cited

U.S. PATENT DOCUMENTS

| | | | | |
|---|---|---|---|---|
| 4,512,466 A | * | 4/1985 | Delang | 206/370 |
| 7,142,118 B2 | | 11/2006 | Hamilton et al. | |
| 7,461,751 B2 | * | 12/2008 | Lyons | 211/85.13 |
| 7,997,847 B2 | * | 8/2011 | Treat et al. | 414/222.01 |
| 2005/0038556 A1 | | 2/2005 | Gagnon et al. | |
| 2005/0215888 A1 | * | 9/2005 | Grimm et al. | 600/426 |
| 2008/0065264 A1 | | 3/2008 | Omura et al. | |

FOREIGN PATENT DOCUMENTS

WO 2009076452 6/2009

OTHER PUBLICATIONS

International Search Report dated Feb. 17, 2012, from corresponding International Application No. PCT/US2011/040483.
International Preliminary Report on Patentability and Written Opinion of the International Searching Authority dated Jan. 3, 2013, from corresponding International Application No. PCT/US2011/040483.

* cited by examiner

*Primary Examiner* — Jonathan Snelting
(74) *Attorney, Agent, or Firm* — Katten Muchin Rosenman LLP

(57) ABSTRACT

A robotic system that identifies surgical instruments, sorts them by type, stores them, and retrieves them for packaging in surgical containers. The system is comprised of robotic components, a surgical instrument input mechanism, a surgical instrument identification system, a machine-vision system to assist in locating and identifying these items, a set of surgical instrument storage bins or stacks, a set of robotically accessible mechanisms for organizing surgical instruments within their containers, and a software control system that allows the device to perform its functions autonomously.

4 Claims, 7 Drawing Sheets

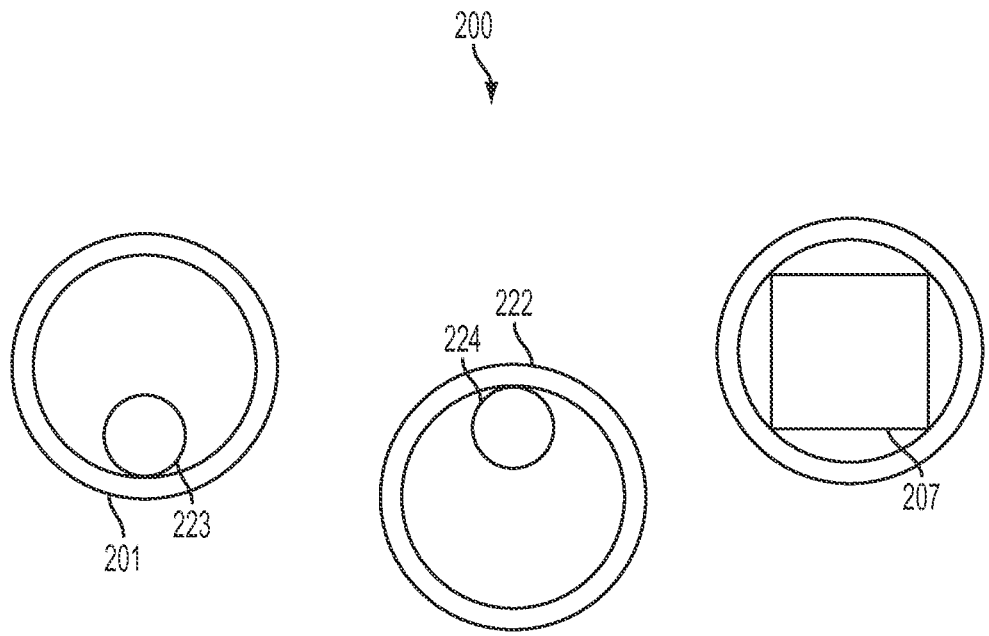
FIG. 2C
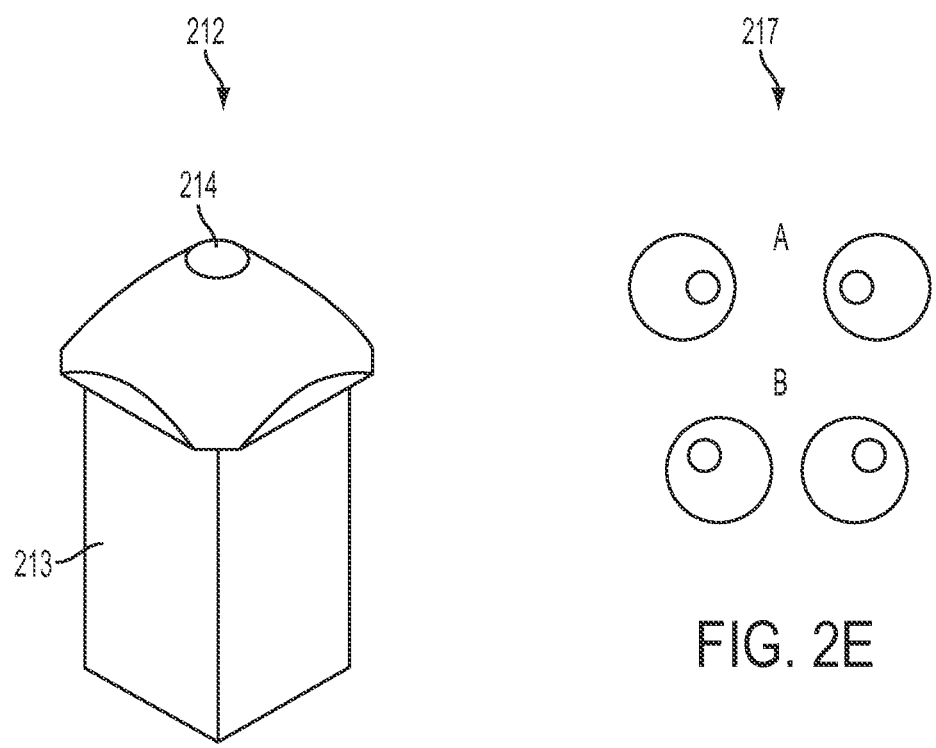
FIG. 2D
FIG. 2E

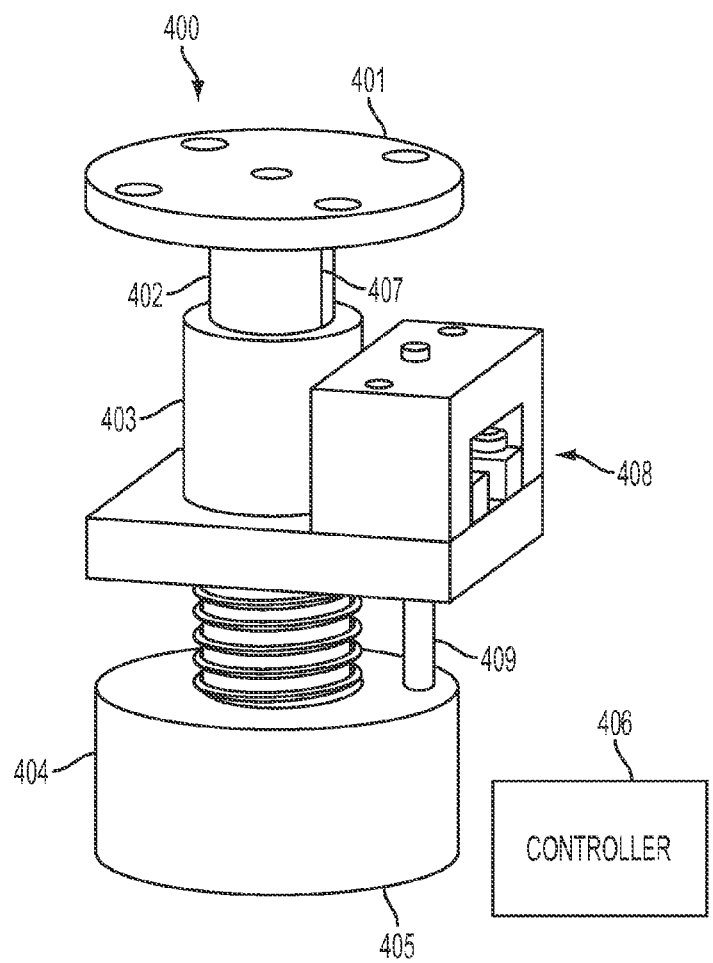
FIG. 4
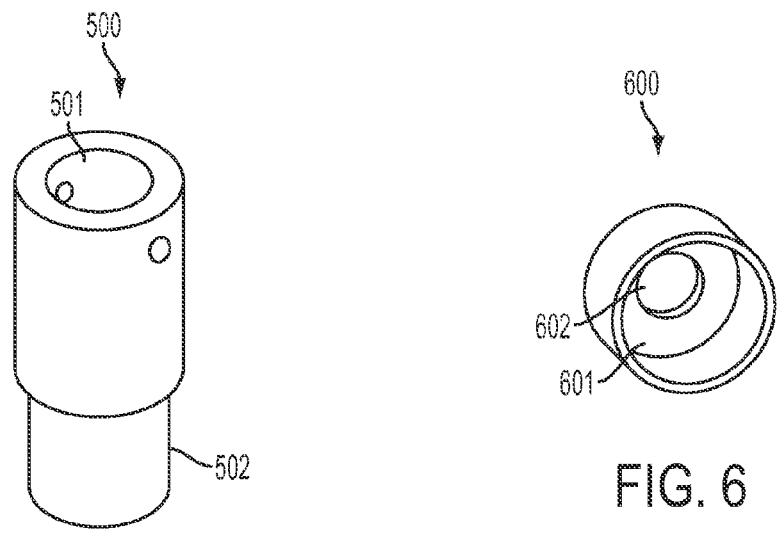
FIG. 5
FIG. 6

AUTOMATED ROBOTIC SYSTEM FOR SURGICAL INSTRUMENT STORAGE AND RETRIEVAL

BACKGROUND OF THE INVENTION

1. Field of Invention

The present invention relates to a system, apparatus, and method for storing, sorting, retrieving, and organizing surgical instruments. More specifically, the present invention relates to an automated system for storing and retrieving surgical instruments for use in surgical procedures.

2. Discussion of Prior Art

With the advancement of medical technology, surgical procedures and their corresponding instruments have become more specialized and numerous. As such, there is a need for an improved system for sorting and storing surgical instruments in a sterile environment, and having these instruments retrieved and presented for their corresponding procedures in an efficient and reliable manner.

SUMMARY OF THE INVENTION

A robotic system, and corresponding method, identifies surgical instruments, sorts them by type, stores them, and retrieves them for packaging in surgical containers. The system is comprised of robotic components, a surgical instrument input mechanism, a surgical instrument identification system, a machine-vision system to assist in locating and identifying these items, a set of surgical instrument storage bins or stacks, a set of robotically accessible mechanisms for organizing surgical instruments within their containers, and a software control system that allows the device to perform its functions autonomously.

BRIEF DESCRIPTION OF THE DRAWINGS

FIGS. 2C, 2D, 2E and 2F illustrate an exemplary stringer mechanism for storing instruments according to the present invention.

FIG. 4 illustrates an electromagnetic gripper component for manipulating instruments according to an exemplary embodiment of the present invention.

FIGS. 5 and 6 illustrate particular elements of the electromagnetic gripper component shown in FIG. 4.

DESCRIPTION OF THE PREFERRED EMBODIMENTS

Figure 1A:
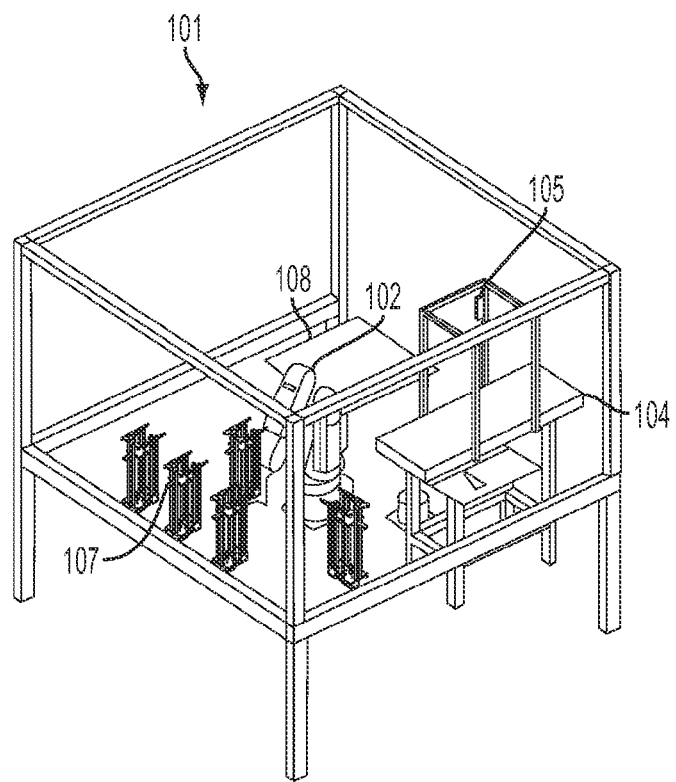
FIGS. 1A and 1B illustrate a perspective view and top-down view, respectively, of an exemplary system workstation in accordance with the present invention.
Figure 1B:
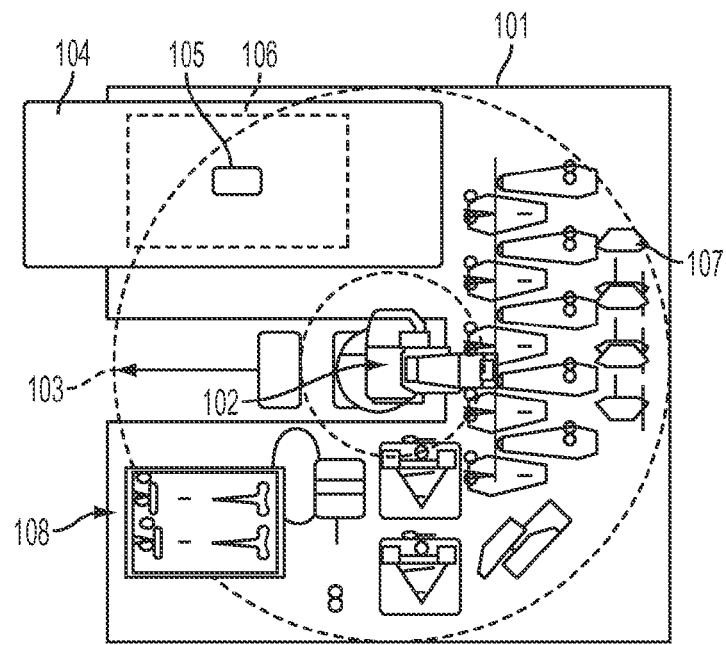

An exemplary perspective view of system workstation 101 is illustrated in FIG. 1A and a top-down view is shown in FIG. 1B. At the center of workstation 101 is a suitably programmed robotic manipulator 102 that preferably has 360° rotation with a lateral reach 103 throughout the workstation 101 to access and manipulate surgical instruments. Instruments are inserted for processing into the robotic workcell's input area 104. Instruments are inserted in a manner such that each instrument can be isolated spatially within the input area 104. Exemplary embodiments of such a mechanism include a conveyor belt, a bed of rollers, or a simple counter top. The location and orientation of each instrument within the input area 104 is determined by an instrument sensor 105 mounted so as to scan a field of view 106 substantially overlapping the input area 104. Exemplary embodiments of such a mechanism include a digital camera or a sonic sensor. The location and orientation emitting from the instrument sensor is used to direct the robotic manipulator 102 to grasp the incoming instruments for further processing.

The system incorporates a method for identifying the surgical instruments by type and/or instance. Exemplary embodiments of such a method include, but are not limited to, barcodes, RFIDs, and machine vision. Instruments entering and identified within the input area 104 are moved into a sorted storage area 107. The area is comprised of storage stacks or bins, each designated to hold one type of surgical instrument or a small predefined number of types. In either case, instruments placed into this sorted storage area 107 are substantially separated by type.

The system can be programmed or commanded at any time to construct a set of surgical instruments as per a count sheet. A count sheet is a list of surgical instrument types and corresponding quantities tailored to meet the requirements of a particular surgical procedure. The system is programmed or commanded to read an electronic version of the specified count sheet and retrieve surgical instruments of the specified types and quantities from the sorted storage area 107. The system is further programmed or commanded to organize those surgical instruments both spatially and in terms of order in an output bay 108. Exemplary embodiments of such organizational mechanisms include robotically accessible surgical instrument stringers or robotically accessible surgical instrument inserts.

In order or organize the surgical instruments for storage and for packaging within a surgical container, the system is able to ascertain the location, orientation, and state of each instrument as it is entered into the system. State of the instrument refers to whether the instrument is closed or opened and to what degree it is opened. This information allows the robotic mechanism to manipulate the instrument with concern for specific features of said instrument and with regard to the auxiliary devices located within in the workcell, as they require specific orientation and placement of the instrument in order to function properly.

Figure 2A:
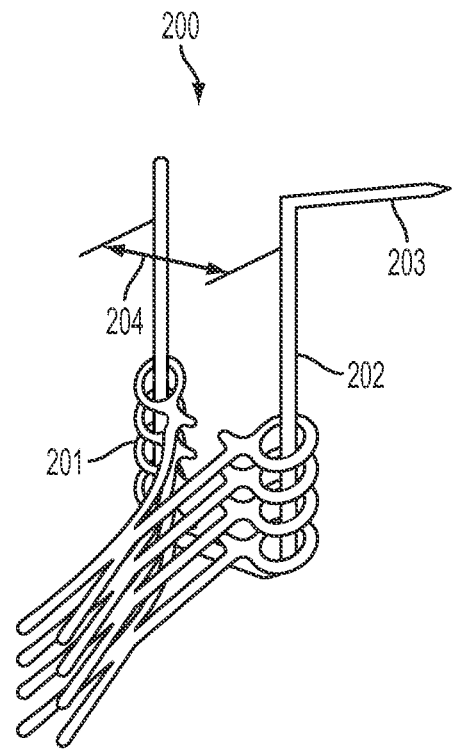
FIGS. 2A and 2B illustrate a mechanism for placing looped instruments in a stringer in accordance with an exemplary embodiment of the present invention.
Figure 2B:
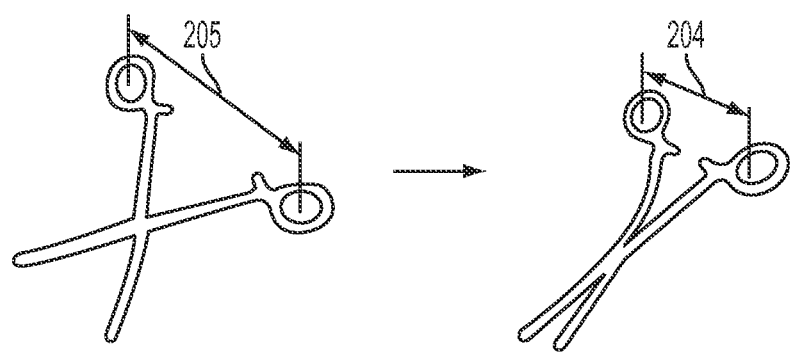

As shown in FIG. 2A and FIG. 2B, looped instruments provide for a particular case where such knowledge is especially useful. During sterilization, looped instruments 201 are placed on a U-shaped stringer 202. The stringer nominally includes a hinged closing bar 203 that secures the instruments on the stringer in the closed position. The separation of the legs of the stringer 202 maintains a separation distance 204 for the loops of the instrument. This distance 204 is great enough that all looped instruments 201 must be in the open (unlocked/unratcheted) position.

The system uses its image sensing capability to determine if a looped instrument is closed, open (and to what degree), or upside down. If the instrument is open to a width 205 that is beyond the width of the stringer, the manipulator places the instrument in a mechanism (not shown) designed to close the instrument to the required distance 204 (FIG. 2B). Proper placement within the closer is required. The system derives the required manipulation of spatial coordinates and orientation of the instrument which will render it in the appropriate location for proper functioning of the closing mechanism. Once in the closer, the instrument is secure. When the closer has finished its operation, the position and orientation of the instrument are known, and the instrument is in a particular open state appropriate for placement on a stringer 202.

The system is able to determine if an instrument is in the closed/ratcheted state using its vision system. If an instrument is closed, the system places it in the instrument opener (not shown). Once again, proper orientation of the instrument is required to ensure the device's functionality. Similarly to the closer, upon completion of the opener's function, the position and orientation of the instrument are known, and the instrument is in an open state suitable for placement on a stringer.

When placed on the stringer prior to sterilizing, it is desirable that the instruments be maintained in an orderly fashion. As such, particularly because some instruments curve upward, it is desirable that all the instruments be placed on the stringer with the appropriate side facing up. Using imaging techniques, the system is able to determine if an instrument is upside down. If so, the manipulator, such as robotic manipulator 102, places the instrument into an instrument flipper (not shown). As in the previous cases, proper orientation of the instrument within the flipper is required for functionality and the location, orientation, and state of the instrument are known after use.

Instrument Storage Device

Looped instruments may be held in the system—for example, in the storage area 107 illustrated in FIGS. 1A and 1B—in specially designed instrument storage devices, termed Elevating Instrument Stringers ("EIS"). FIGS. 2C, 2D, 2E, and 2F illustrate exemplary elements of an EIS.

Elevating Instrument Stringers (EIS) Stringer Rods

Typical instrument stringers are constructed from ¼" (6.3500 mm) diameter stainless steel rod. This is considerably smaller than the smallest characteristic loop diameter and allows for ease of placement when loading a stringer. Because of the difference in diameter, the position of the instrument can vary relative to the stringer (200). If the position of the center of the stringer rod is known to the system, the center of the instrument loop can vary in any direction by the difference between the radius of the instrument loop (201, 222) and the radius of the stringer rod (223, 224), as illustrated in FIG. 2C.

Figure 2F:
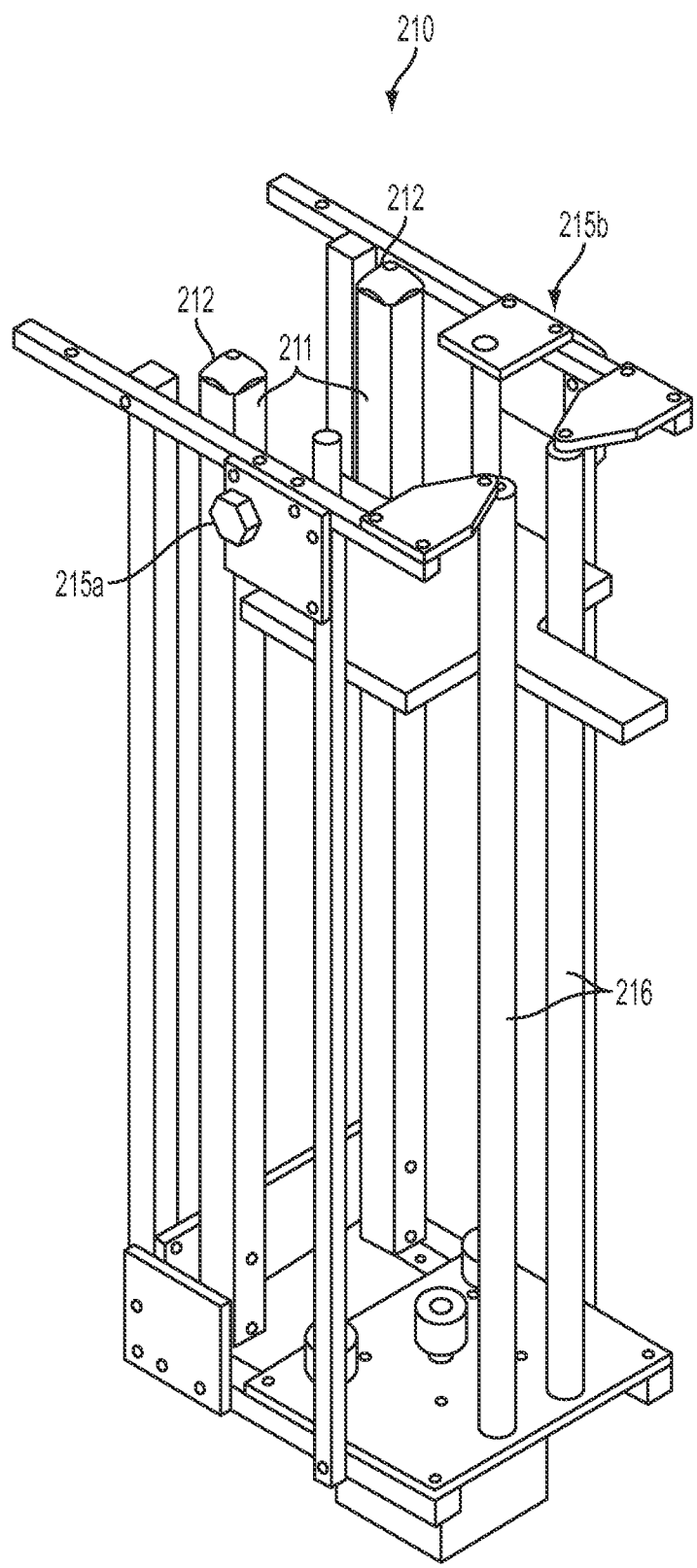

As a primary goal of the EIS (210), as shown in FIG. 2F, is to maintain the position of the instruments loaded on to it, stringer rods (211) which minimize the variable location of the instruments are desired. As such, the EIS may employ a stringer rod with a larger effective radius (207), as illustrated in FIG. 2C. A preferred embodiment of the EIS has stringer rods made from ½" (12.700 mm) square Aluminum tubing with ¹⁄₁₆" (1.5875 mm) walls, though other shapes and sizes could be used. This size permits a looped instrument with characteristic loop diameter of 0.7.

In standard use, the robotic manipulator moves instruments from the EIS to a typical instrument stringer. If the centers of both the EIS stringer rod and the instrument stringer are known, and the loop of the instrument is around the larger effective stringer, the movement to the smaller diameter is given a tolerance. That tolerance is equal to the difference between the effective diameter of the large stringer rod minus that of the smaller rod.

In standard use, the robotic manipulator also moves instruments from one EIS to another. Because every EIS stringer rod has the same effective diameter, moves between them would have zero tolerance. To induce tolerance into these moves, the EIS stringer rods have placement cones (212) inserted into the top of the ½" (12.700 mm) square tubing of the stringer rods (211). FIG. 2D illustrates details of an exemplary placement cone (212). The cones (212) are made of plastic and have a square stem (213) with a cross section slightly greater than the inner dimensions of the tubing. In the preferred embodiment, that profile is a ⅜" square. The induced tolerance is equal to the effective diameter of the EIS stringer rod minus the diameter at the tip (214) of the placement cone. A preferred embodiment of the placement cone has a 45 degree angle and a tip diameter of ⅛" (3.1750 mm).

EIS IR Sensor/Emitter

Referring back to FIG. 2F, in order to maintain the top instrument at a consistent height, a preferred embodiment of the EIS 210 incorporates an infrared (IR) emitter/sensor pair (215a & b). They are placed on opposite sides of the EIS with the emitter pointed towards the sensor. The sensor is a transistor with a base activated by IR radiation. The effects of the emitter on the sensor are interpreted by a controller—for example, controller 307 illustrated in FIG. 3.

The emitter/sensor pair is used for both the placing and removing of instruments. When an instrument is placed on the stack, it obstructs the IR beam. The stack is then lowered until the beam is revealed to the sensor. When an instrument is removed from the stack, the stack is raised until the top instrument again obstructs the beam.

EIS Adjustable Instrument Guides

An aspect of the design of many looped instruments is a gradual thickening proceeding from the loops to the tip. When the instruments are stacked very neatly, the result is each successive instrument on the stack angling more and more upwards towards the tip. In more haphazard stacks the instruments do not align perfectly, and the tips tend to displace laterally. The result in this case is the opposite, and as the stack grows successive instruments tend to angle downwards.

The goal of the Instrument guides (216) is to maintain the instruments in a stacked state between these two extremes e.g., a level stack. By limiting the lateral displacement near the hinge of the instrument, the stack will tend to angle less downward. Too great a restraint on the lateral displacement, however, and the instruments will resemble the neat stack and angle upwards. The goal is to produce a somewhat haphazard stack where the instruments stack more or less flat.

Due to variations in geometry, different instrument types behave differently when stacked. With regards to achieving a flat stack of instruments, different instruments require the restricting surfaces of the guides to be at different distances. In order to achieve a consistent design, the preferred embodiment uses instrument guides which may be adjusted. The adjustment is achieved by offsetting the threaded mounting holes (217) of the guide (216), as illustrated in FIG. 2E. The result is similar to a cam. To adjust the distances, the attachment screws are loosened, and the guide is spun around. Depending on the angle of rotation, the distance between the two surfaces will be larger (217 A) or smaller (217 B). In the preferred embodiment, a ⅜" (9.5250 mm) aluminum rod is used with the mounting hole offset from center by ³⁄₃₂" (2.3812 mm), allowing for the distance between the two surfaces to vary continuously over a ⅜" (9.5250 mm) range (217). In the preferred embodiment, the center of the rods are located so as to correspond with the joint of the looped instruments. As the distance from the loops to the joint varies depending on instrument type, the distance is an approximation of the average, and is roughly 3¾ (95.250 mm) inches. The surfaces of the instrument guides (216) are 1 inch (25.400 mm) apart at their nearest location, but other distances may be used.

Figure 3:
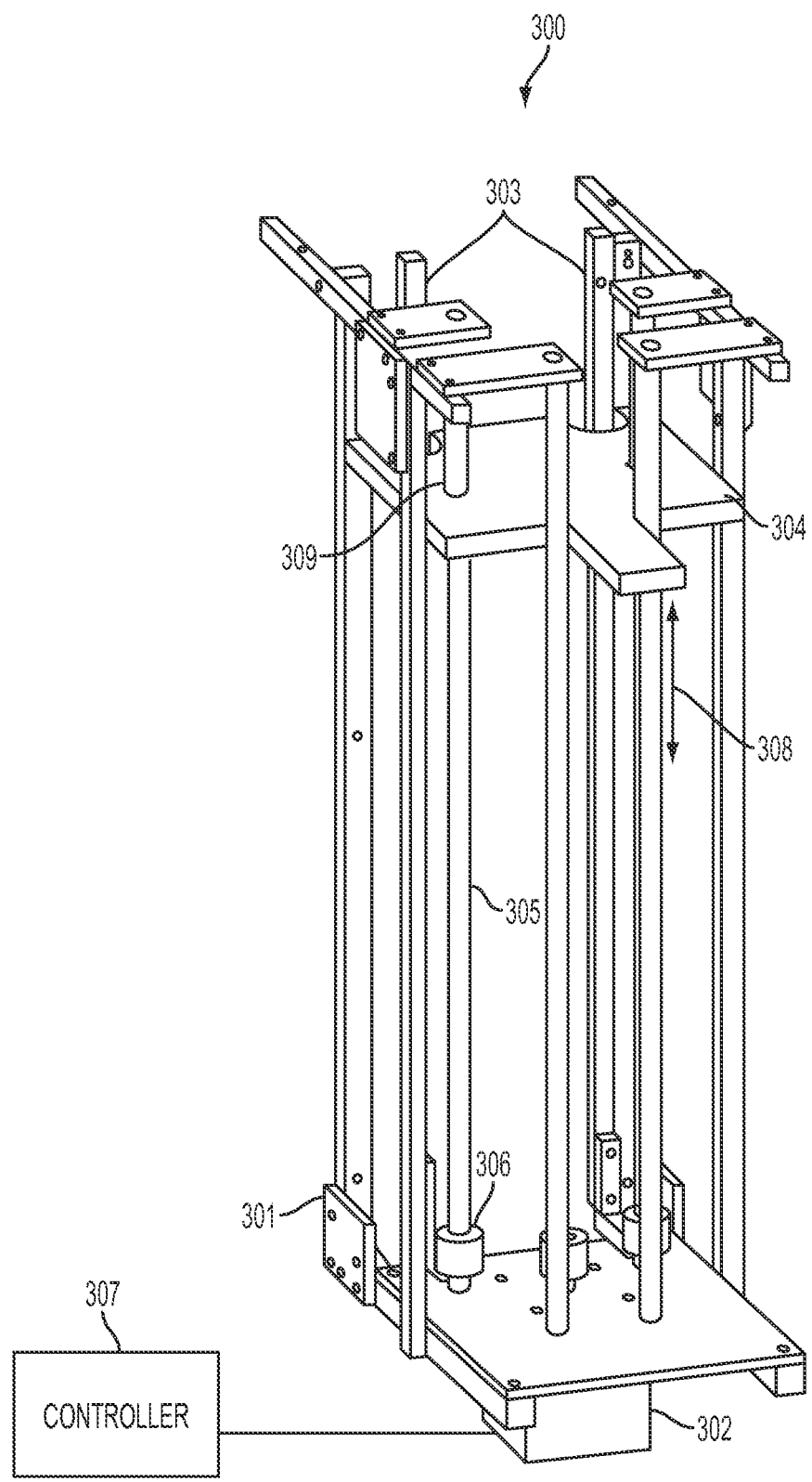
FIG. 3 illustrates another exemplary stringer mechanism for storing instruments according to the present invention.

FIG. 3 illustrates an EIS device (300) according to another exemplary embodiment of the invention. Essential elements of the device include a body (301), an actuator (302), Stringer rods (303), instrument platform (304), lead screws (305), a drivetrain (306), and a controller (307).

The goal of the present invention is to maintain significant quantities of looped instruments within reach of the robotic manipulator, such as robot arm 102, and to do so with a known type, instance, position, orientation, and state.

The EIS may be used in either a heterogeneous or homogeneous manner. That is, the EIS may be used to hold any number of different types of instruments, or may be used to hold only one type.

In operation, the EIS functions by raising and lowering (308) the instrument platform (304). This is accomplished through activating the actuator (302), which is connected to the lead screws (305) through the drivetrain (306). In a preferred embodiment of the device, the actuator (302) is a stepper motor, the drivetrain (306) consists of timing belts and pulleys, and the lead screws (305) are made of stainless steel and have standard ¼ (6.3500 mm) 20 right hand thread. The lead screws (305) mate with threaded inserts (309) embedded in the instrument platform (304). Clockwise rotation of the motor induces clockwise rotation of the lead screws (305), and results in the platform (304) lowering. The controller (307) determines the number of steps that should be taken.

Any type of looped instrument may be placed into the EIS. The instrument most recently inserted into the EIS is the only one accessible to the robotic manipulator and is maintained in the top position. The top position may be defined as the location occupied by a single instrument when the instrument platform (304) is in its highest position. When a new instrument is added to the EIS, the instrument platform (304) is lowered to allow for the newly inserted instrument to occupy the top position. When an instrument is removed, the platform (304) is raised, bringing the next instrument to the top position.

If the type of instrument being placed into EIS is known, the controller (307) will command that the platform (304) be lowered by a distance corresponding to the effective thickness of the instrument. If the type of instrument is not known, the platform will be lowered by a standard amount. The same concept applies to known and unknown instruments being removed from the EIS, and the ensuing raising of the platform (304). In either event, the lowering and raising of the platform (304) may be controlled according to the emitter/sensor pair (215a & b), as described above. This allows for more accurate maintenance of the top position.

Instruments are placed into the EIS such that each stringer rod (303) goes through one of the loops of the instrument. A preferred embodiment of the device has the center of the stringer rods 2½ inches (63.500 mm) apart, but any distance may be used.

Instrument stringers typically used in surgery are constructed of Stainless Steel and are ¼ (6.3500 mm) inch diameter. The EIS may use but is not limited to stringer rods of similar construction. The cross sectional shape of the stringer rods may be square or any other shape. The characteristic dimension of the stringer rods may be larger. As the loops of the instruments are much larger than ¼ inch (6.3500 mm), using larger stringer rods will allow for tighter tolerances of instrument location.

Electromagnetic Gripper

Looped instruments are made from magnetic stainless steel. Their shape is difficult to handle with typical robotic grippers and their features are generally too small for suction type grippers. A controllable electromagnetic gripper presents the most capable way of manipulating looped surgical instruments, and that is the method used on PenelopeCS.

A preferred embodiment of the electromagnetic end effector (400) is seen in FIG. 4. Major components of the gripper include a mounting flange (401), an upper body (402), a lower body (403), a rejection hood (404), an electromagnet (concealed by rejection hood) (405), and a controller (406).

Different instances of instrument picks require different magnetic strengths. The preferred embodiment of the gripper incorporates a Pulse Width Modulation (PWM) power control to vary magnet strength. PWM is defined by a period and a duty cycle, with the duty cycle signifying the percentage of the period for which power is supplied. The present embodiment uses a period of 1 ms and a duty cycle ranging from zero to 100 percent. The PWM is commanded by the controller.

Surgical instruments vary in thickness. The workspace which the robotic manipulator works within is large, and it is difficult to achieve precise height consistency over such a large distance. The stacks of the instruments may be angled in such a way that the instruments are higher than what the robotic manipulator expected. For these reasons, the preferred embodiment of the electromagnetic gripper incorporates a design consisting of an upper and a lower body which are coupled with a spring. The Upper body is stationary relative to the robotic manipulator. The lower body (403, 500), shown in isolation in FIG. 5, is connected to the upper body (402) with a pin or screw which traverses a slot (407) cut in the upper body (402). The slot and pin prevent axial rotation while allowing for vertical displacement. A well (501) through the lower body (403, 500) houses a spring, which presses against the bottom of the upper body (402). Under nominal conditions, the spring forces the pin to the bottom of the slot. When the gripper encounters something at a higher elevation then anticipated, the spring compresses to make up the difference.

When a magnet interacts with a magnetic metal, the magnetic structure of the metal remains affected even after the magnet is removed. This is referred to as residual magnetism. When the robotic manipulator is ready to release an instrument, the PWM duty cycle of the magnet is set to zero. However, residual magnetism in both the magnet structure and instrument can overcome the force of gravity on the instrument and result in the instrument "sticking" to the magnet.

To combat the "sticking" effect, the preferred embodiment of the electromagnetic gripper incorporates a rejection hood (404, 600), shown in isolation in FIG. 6. The form of the rejection hood is cylindrical with several characteristic dimensions. In a preferred embodiment, the outside diameter is 1.5" (38.100 mm). A primary feature is a large hole (601) with a diameter equal to the magnet and with a depth 0.1" (25.400 mm) greater than the height of the magnet. The depth is slightly greater so that the rim of the rejection hood hangs slightly below the surface of the magnet. Another feature is a through hole (602) with a diameter equal to the diameter of the lower portion of the lower body (403, 500). The lower portion of the lower body has a reduced diameter (502) to house a spring which applies force to the rejection hood.

When the magnet grips an instrument, the magnetic force is strong enough to overcome both the gravitational weight of the instrument, as well as the spring force maintaining the position of the rejection hood. When holding an instrument, the rim of the rejection hood is coplanar with the surface of the magnet and the instrument is touching the magnet. When the magnet's duty cycle is set to zero, the combined forces of gravity and the spring applying force to the rejection hood overcome the "sticking" force of the residual magnetism, and the instrument is released.

The electromagnetic gripper incorporates an instrument presence switch (408). The shaft of the switch (409) is displaced by the top of the rejection hood when an instrument is present on the magnet. The switch is a normally closed (NC) switch. An NC switch has the advantage of becoming open with very little displacement of the switch shaft. As most switches use a spring to maintain the position of the switch shaft, the further the shaft must be displaced the greater the restoring force of the spring. It is desired to impose as little force on the rejection hood as possible. An NC switch is preferred, but a normally open switch could also be used assuming a low strength spring.

Stringer Holders

Figure 7:
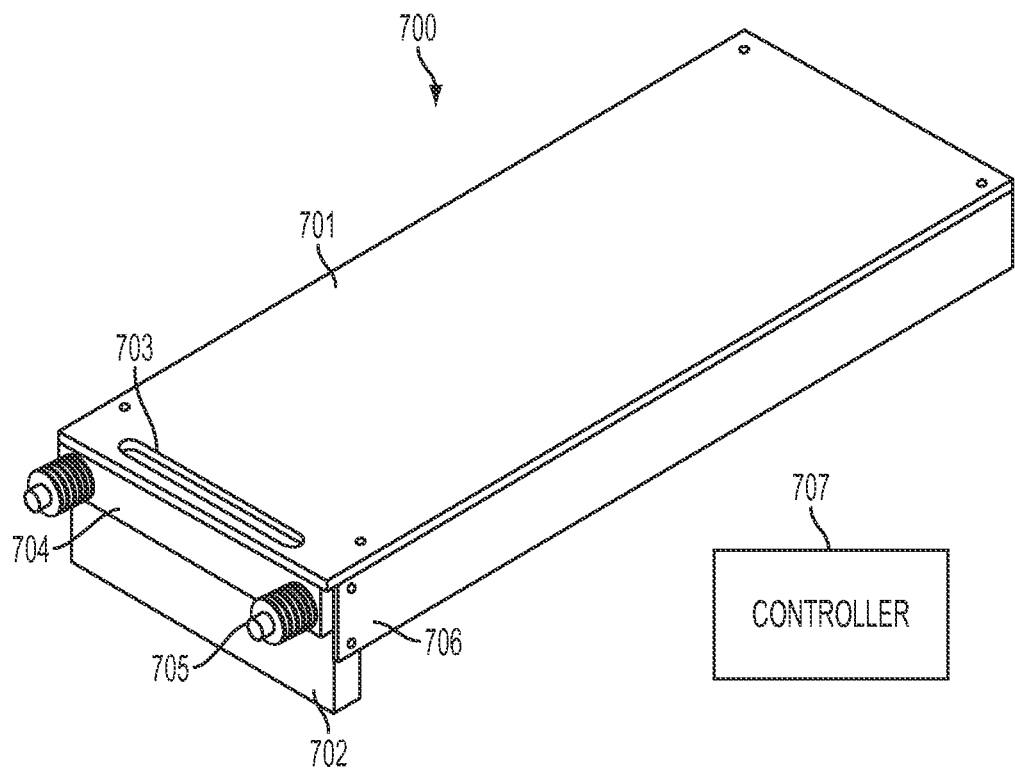
FIG. 7 illustrates a device for accepting and holding a surgical instrument stringer in accordance with an exemplary embodiment of the present invention.

Referring now to FIG. 7, the present invention is also directed to a device (700) for the accepting and holding of a surgical instrument stringer—for example, at output bay (108) for assembling an output grouping. Primary components of the device (700) include a body (701), a holding block (702), an insertion slot (703), a compression strip (704), a compression mechanism (705), a stringer presence switch (706), and a controller (707).

Figure 8:
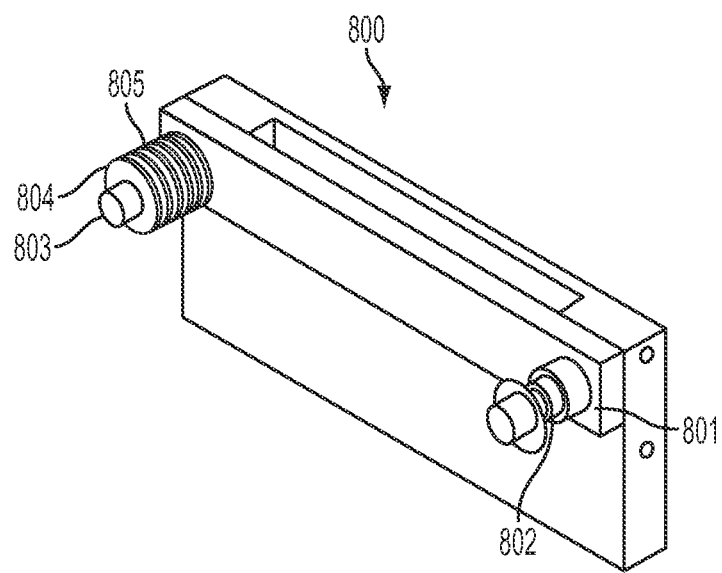
FIG. 8 illustrates particular elements of the device shown in FIG. 7.

The compression mechanism (705) applies a linear force on the compression strip (704) towards the holding block (702). The assembly (800) in FIG. 8 illustrates this operation in detail. The linear action occurs between a Teflon bushing (801) and a ¼" (6.3500 mm) stainless rod with internal 8-32 threads called the sliding rod (802). The sliding rod is secured to the holding block with an 8-32 screw. The bushings are fitted to the compression strip. An adjusting screw (803) and a washer (804) hold a spring (805) in place which forces the compression strip towards the holding block. The springs may be pre-tensioned to a desired degree by turning the adjusting screw (803).

The insertion slot is demarcated by the opposing faces of the compression strip and the holding block. The face corresponding to the holding block is recessed into the holding block. The depth of the recession determines the nominal width of the insertion slot.

In order for the compression force to hold the stringer in place, the nominal width of the insertion slot is slightly less than the stringer. For the present invention, the accepted stringer diameter is ¼" (6.3500 mm), though the design can be altered for smaller or larger diameters. As such, the nominal width of the slot is approximately 0.23" (5.8420 mm). A common stringer has legs with centers 2.5" (63.500 mm) apart resulting in a total width of 2.75" (69.850 mm). As such, the length of the slot is slightly longer than 2.75" (69.850 mm), but the design could be altered to accept different sizes.

In use, a stringer is placed at the top of the slot. Then the user applies a force down until the compression strip slides away from the holding block allowing the stringer to enter the slot. The user continues to push the stringer down until it reaches the bottom of the slot. The strength of the compression springs squeezing the stringer between the compression strip and the holding block create sufficient friction to ensure that the stringer will remain stationary when released. The strong springs also maintain the position as instruments are added. The springs combined with the constraining effects of the precise slot dimensions ensure that the stringer will be in consistent position not just for one use, but for repeated uses. This feature allows the device to be used in robotic applications.

A preferred embodiment of the present invention incorporates a stringer presence switch. The actuator for the switch lies at the center of the bottom of the slot. This position is chosen to ensure that the stringer is completely inserted, and not angled. This is particularly important for robotic application where the consistent location of the stringer is required. The state of the switch is interpreted by the controller (707).

Description of Method

The system described above is designed to be used as part of a new and improved method for storing and retrieving surgical instruments. The method offers considerable advantages over the current system.

One of the advantages is that space is used both for the process of producing the output groupings of surgical instruments, and also for the storage of these instruments. In the current manual system, the instruments are stored in bulky cabinets or on peg boards along the walls of the sterile supply department. These instruments are manually taken out of the cabinets or from the pegboards and then have to be laid on a large table in order to be sorted and placed in a preferred output grouping, such as a stringer. The new system provides for both storage and assembly of output groupings, in effect getting more use from the space than the old system.

Another advantage is that the production of output groupings can be done automatically, without any input from the workers in the sterile supply department. The sterile supply worker needs to only load the system with instruments, without even knowing exactly how many or what type he/she is inputting to the system. The system then, on its own time, goes about the task of producing output stringers, according to a predetermined plan or schedule, that may be based on the schedule of the operating room that day.

Another advantage relates to the elimination of errors that result from manually building each output grouping or stringer. This is a more difficult job than many people realize. It is a repetitive and demanding job to perform all the steps required to build a correct stringer. Each stringer will typically have several different types of instruments, and there will be up to a dozen of each type. These stringers must contain exactly the right number and types of instruments, otherwise, errors in the final count can occur in the operating room. Since thousands of instruments must be identified, sorted, counted and placed onto stringers every day in the sterile supply department, it is easy to see how there is ample opportunity for human errors to take place. The system eliminates these errors by automatically performing the identification, sorting, counting and assembling of stringers.

Another advantage of the system relates to immediate availability of correctly loaded stringers. This happens since the system can be building stringers on its own time, and simply keeping them waiting to be taken out by the worker when needed. Thus, there is effectively no delay between receiving notice from the Operating Room ("OR") that a certain type of stringer is going to be needed soon, and having that stringer available, provided that the system has been instructed to produce these types of stringers. In practice, this is easy to do, since it is usually known in advance what types of surgical cases are going to be done on the present day or the next day. This information can be programmed into the system and it can assemble the correct stringers and have them ready and waiting.

Instruments that have been decontaminated and cleaned are loaded one by one into the system by the worker. The system then automatically identifies each instrument and puts it into a special storage area, the elevating instrument stringers described above. Once the worker has loaded available clean instruments into the system, no further intervention is required and the worker is free to do other jobs that need to be done. The system, acting on predetermined programming, will then build stringers of the required type (i.e. number and type of individual instruments).

The system can output whole stringers with predetermined numbers and types of instruments. It can automatically build a certain number of these every day. It can also respond to immediate request for entire stringers or for just single instruments, much like a vending machine.

The inventor describes exemplary embodiments of the invention with particular conditions to aid the reader in understanding the invention and the concepts contributed by the inventor to furthering the art. And the inventor does not intend to limit the invention to such specifically recited examples and conditions, nor does the organization of such examples in the specification relate to a showing of superiority and inferiority of the invention. Although the embodiments of the present invention have been described in detail, it should be understood that various changes, substitutions, and alternations could be made hereto without departing from the spirit and scope of the invention

The invention claimed is:

1. A system for storing and retrieving surgical instruments, said system comprising:
   an automatic storage apparatus that comprises:
      a storage area that stores a plurality of instruments of one or more types;
      a robotic manipulator that manipulates the plurality of instruments; and
      a sensing mechanism for determining one or more of a type, an instance, a position, an orientation, and a state of openness of the plurality of instruments; wherein
   all of the plurality of instruments are within reach of the robotic manipulator for retrieving one or more of the plurality of instruments, and
   the robotic manipulator retrieves the one or more of the plurality of instruments to form an output grouping of instruments,
   wherein the automatic storage apparatus further comprises one or more sets of mechanized elevating instrument stringers in the storage area for holding the plurality of instruments,
   wherein each set of the mechanized elevating instrument stringers are comprised of a body, an actuator, stringer rods, an instrument platform, lead screws, a drivetrain, and a controller.

2. The system of claim 1, wherein the mechanized elevating instrument stringers have special adjustable instrument guides to accommodate different sizes of instruments.

3. The system of claim 1, wherein the mechanized elevating instrument stringers have an infrared (IR) emitter/sensor pair to detect a presence and an absence of the plurality of instruments.

4. The system of claim 1, wherein the automatic storage apparatus further comprises a stringer holder, said stringer holder comprising:
   a body,
   a holding block,
   an insertion slot,
   a compression strip,
   a compression mechanism,
   a stringer presence switch, and
   a controller, and
   the automatic storage apparatus loads one or more non-mechanized stringers automatically with instruments according to a predetermined plan.

* * * * *